United States Patent [19]

Shah

[11] Patent Number: 5,478,816
[45] Date of Patent: Dec. 26, 1995

[54] LIQUID VITAMIN FORMULATIONS CONTAINING VITAMIN D ESTERS

[75] Inventor: Mandar V. Shah, Evansville, Ind.

[73] Assignee: Bristol-Myers Squibb Company, Del.

[21] Appl. No.: 86,784

[22] Filed: Jul. 2, 1993

[51] Int. Cl.[6] ................................................. C07C 401/00
[52] U.S. Cl. ................................ 514/167; 514/168
[58] Field of Search .................................. 514/167, 168

[56] References Cited

U.S. PATENT DOCUMENTS 2,758,923  8/1956  Wakely .

OTHER PUBLICATIONS

D. R. Fraser and E. Kodicek, "Enzyme Studies on the Esterification of Vitamin D in Rat Tissues," *Biochem. J.*, 109, 457–467, 1968.

W. Huber and D. W. Barlow, "Chemical and Biological Stability of Crystalline Vitamins $D_2$ and $D_3$ and Their Derivatives," *J. Biol. Chem.*, 149, 125–137, 1943.

Matthew G. Silva, et al., "Reversed-Phase Liquid Chromatographic Determination of Vitamin D in Infant Formulas and Enteral Nutritionals," *Journal of AOAC International*, 75(3), 566–571, 1992.

Miloslav Rechcigl, Jr., Editor, *Handbook of Nutritive Value of Process Food*, vol. 1, "Food For Use," CRC Series in Nutrition and Food, 1982.

*Primary Examiner*—Kimberly J. Kestler
*Attorney, Agent, or Firm*—Thomas R. Savitsky

[57] ABSTRACT

Liquid vitamin formulation containing an ester of antirachitic vitamin D esterified at the 3 carbon position such as vitamin $D_3$ palmitate, greater than 252 mg/ml water and at least about 100 mg/ml polyhydroxylated solvent such as glycerine. The formulations have improved taste and improved storage stability.

32 Claims, No Drawings

LIQUID VITAMIN FORMULATIONS CONTAINING VITAMIN D ESTERS

FIELD OF THE INVENTION

The present invention concerns liquid vitamin formulations containing esters of vitamin D.

BACKGROUND OF THE INVENTION

Current liquid vitamin formulations contain relatively low amounts of water. Such formulations suffer from poor taste or palatability and high osmolality. The water content in such formulations is low due to the putative instability of some vitamins such as vitamin D. Vitamin $D_2$ has been shown to deteriorate in propylene glycol when diluted in water; however, it has been taught to be stable in corn oil, propylene glycol, and milk (Tractor Jitco, Inc.: Scientific literature reviews on generally recognized as safe (GRAS) food ingredients—Vitamin D, PB-234 901, U.S. Dept. Commerce, July 1974; W. Huber and O. W. Barlow, "Chemical and Biological Stability of Crystalline Vitamins $D_2$ and $D_3$ and Their Derivatives," *J. Biol Chem.*, 149, 125–137, 1943).

It is taught in the art that vitamin D is slowly destroyed in an alkaline medium or in the presence of light and air, and that it is stable at a mid-pH (M. Rechcigl, Jr., Ed., *Handbook of Nutritive Value of Processed Food*, Vol. I, "Food for Human Use," CRC Series in Nutrition and Food, 1982). It has also been disclosed that vitamin D is unstable in the presence of minerals (U.S. Pat. No. 2,758,923) and in an aqueous environment (D. R. Fraser and E. Kodicek, "Enzyme Studies on the Esterification of Vitamin D in Rat Tissues," *Biochem. J.* 109, 457–467, 1968).

Liquid vitamin formulations currently commercially available include Poly-Vi-Sol® available from Mead Johnson Nutritionals, Evansville, Ind., U.S.A., and Polyvitamin Drops available from Rugby Laboratories. Increasing the water content will typically result in marked instability of vitamin D upon storage. Although the palatability of such a formulation is markedly improved with increased water content, the instability of vitamin D renders such a formulation commercially unfeasible. This problem has been solved by the present invention through the use of an ester of vitamin D.

SUMMARY OF THE INVENTION

The present invention is directed to a liquid vitamin formulation at an acidic pH comprising an ester of vitamin D, greater than 252 milligrams/milliliter (mg/ml) water, and at least about 100 mg/ml polyhydroxylated solvent.

DETAILED DESCRIPTION OF THE INVENTION

As used herein, the term "vitamin D" shall mean any of the antirachitic forms known in the art to be suitable for nutritional use such as vitamin $D_1$, vitamin $D_2$, vitamin $D_3$, vitamin $D_4$, vitamin $D_5$, vitamin $D_6$, and vitamin $D_7$. Preferred is vitamin $D_3$. The structure of vitamin $D_3$ is shown below with each carbon atom being numbered.

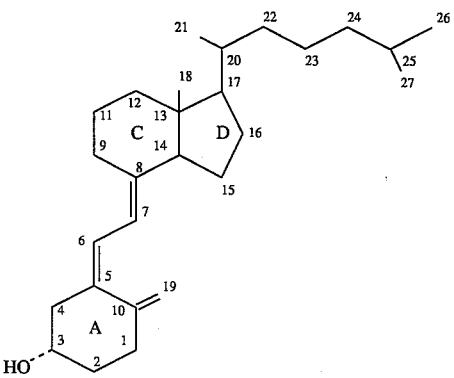

As used herein, the term "vitamin D activity" shall mean activity as determined in accordance with the HPLC procedure described in Example 3 hereof.

Various forms of non-esterified vitamin D are useful to prepare the esters of the invention such as those wherein the side chain (carbons 20–27) is modified. The vitamin D esters of the present invention are those wherein the hydroxyl group of carbon 3 is esterified with any esterifying acid suitable for use as food. As used herein, the term "ester" means a compound formed by the reaction of an acid and an alcohol with the elimination of water. The acid used to prepare the ester may be a $C_1$ to $C_{22}$, preferably $C_2$ to $C_{16}$, organic acid or an esterifying inorganic acid. Such organic acids are saturated or unsaturated aliphatic acids or aromatic acids and optionally contain additional functional groups such as amino, hydroxy, carboxy, and the like. Thus, the organic acids can be amino acids such as glycine or alanine; fatty acids such as acetic, octanoic or palmitic acids; hydroxylated acids such as lactic acid; acidic microbial inhibitor acids such as sorbic or benzoic acids or dicarboxylic acids such as succinic or fumaric acids. The acids may also be non-carboxylic acids such as sulfonic acids, phosphoric acids, or the like. Esterifying inorganic acids may also be used to form such esters as vitamin D sulfate, vitamin D phosphate, or the like. However, organic acids are preferred and fatty acids are most preferred. Fatty acid moieties of the invention can contain one to 22 carbon atoms, preferably 2 to 20 carbon atoms, more preferably 8 to 18 carbon atoms, and most preferably 14 to 18 carbon atoms. The fatty acid moieties are saturated or unsaturated. Specific examples of vitamin D esters useful herein include vitamin D acetate, vitamin D propionate, vitamin D caproate, vitamin D caprate, vitamin D laureate, vitamin D myristate, vitamin D palmitate, vitamin D stearate, vitamin D oleate, vitamin D linolenate, Vitamin D arachidonate, vitamin D linoleate, vitamin D eicosapentaenoate, vitamin D docosahexaenoate, vitamin D benzoate, vitamin D lactate, vitamin D sorbate, vitamin D glycinate (alpha-amino acetate), vitamin D alanate (alpha-amino propionate), vitamin D succinate, vitamin D fumarate, vitamin D polyethylene glycol succinate, or a mixture thereof. Especially preferred are esters of vitamin $D_3$. Vitamin $D_3$ palmitate is most preferred.

The amount of the ester of vitamin D present in the formulation of the invention provides per milliliter (ml) of total Composition typically about 100 International Units (IU) to about 2000 IU, preferably about 200 IU to about 1000 IU, and more preferably about 360 IU to about 800 IU.

Vitamin D esters of the invention can be prepared by methods known in the art or taught herein, for example, the acid halide, preferably the acid chloride (e.g. sulfonyl chloride, phosphoryl chloride, fatty acid chloride or the like) is reacted with the desired form of non-esterified vitamin D under Schotten-Baumann conditions using a strong base such as sodium hydroxide or under Einhorn conditions using a milder base such as pyridine. Other suitable esterification techniques can also be used such as using an appropriate dehydrating agent such as carbodiimide and the like. An example of reacting the desired form of non-esterified vitamin D with the desired fatty acid chloride is disclosed in *Khim-Farm. Zh.* 25(9), 65–67, 1991.

The formulations of the invention have an acidic pH. Typically, the pH of the formulation is about 6 or less, preferably between about 3 and about 6 and more preferably between about 3.2 and about 5.6. The pH of the formulation is typically controlled by adjusting the ratio of ascorbic acid to the salt of ascorbic acid.

The composition of the invention also contains a polyhydroxylated solvent such as glycerine, sorbitol, polyethylene glycol, and the like. Of course, the polyhydroxylated solvent must be suitable for oral consumption and mixtures of such solvents can be used. The amount of polyhydroxylated solvent can vary although it is typically substantial, for example, about 100 mg/ml or more of the total formulation. A preferred amount of polyhydroxylated solvent is about 500 to about 950 mg/ml of total composition, more preferred is about 550 to about 850 mg/ml. Glycerine is the most preferred polyhydroxylated solvent.

The amount of water in the formulation is greater than 252 mg/ml of total formulation. Increasing the water content, for example to 320 mg/ml or greater, will improve the taste of the formulation. The amount of water in the formulation of the invention will typically vary between about 280 and about 550 mg/ml of total composition. Preferred amounts of water in the composition of the invention are about 320 to about 550 mg/ml, more preferred is about 320 to about 450 mg/ml, even more preferred is about 350 to about 430 mg/ml, and most preferred is about 370 to about 410 mg/ml.

The increased water content of the formulation of the invention reduces osmolality. For example, increasing the water content of a formulation of the invention from 252 to 390 mg/ml reduces osmolality from 8390 to 7410 mOsm/kg. This reduced osmolality improves the taste of the product and improved patient tolerance. Osmolality of the vitamin formulation of the invention is typically about 7000 to about 9000 mOsm/kg.

The composition of the invention typically contains one or more other vitamins such as thiamine, riboflavin, niacin, vitamin $B_6$, vitamin C, vitamin $B_{12}$, vitamin A, vitamin E, and the like. When present, such other vitamins are typically present in an amount of at least about 80% of the U.S. Recommended Daily Allowance (RDAs) per dose of composition, more typically at least about 90% of the RDAs per dose of composition, and preferably at least about 100% of the RDAs per dose of composition. It is recognized that the daily dose recommended by nutritional experts may change. A typical dose of composition is one milliliter. The current RDAs for selected vitamins are as follows:

| vitamin A | 1500 IU |
|---|---|
| vitamin D | 400 IU |
| vitamin E | 5 IU |
| vitamin C | 35 mg |
| thiamine | 0.5 mg |
| riboflavin | 0.6 mg |
| niacin | 8 mg |
| vitamin $B_6$ | 0.4 mg |
| vitamin $B_{12}$ | 2 µg |

Those skilled in the art appreciate that appropriate additional amounts (overages) of vitamin ingredients need to be provided to compensate for some loss during storage of the vitamin formulation.

The vitamin formulation of the invention can be prepared by standard techniques known in the art. As appreciated by the skilled artisan, the desired processing technique will vary depending upon the exact types and amounts of vitamins present, nature and amount of surfactant, processing temperature, and the like.

The vitamin formulation of the invention can also contain flavorants such as fruit and/or other similar flavors, caramel, and the like. When present, flavorants are typically present in an amount of about 0.005 to about 0.3 mg/ml, more typically about 0.05 to about 0.1 mg/ml.

The vitamin formulation of the invention typically contains one or more surfactants such as polyoxyethylene sorbitan fatty acid esters (e.g., polysorbate 20, 40, 60 and 80), polyethylene glycol ethers of n-alkanol (e.g., BRIJ 58), and the like. The most preferred surfactant is polysorbate 80. The amount of surfactant is typically about 1 to about 100 mg/ml of total formulation with about 5 to about 50 mg/ml being more typical.

The vitamin formulation of the invention optionally can also contain other ingredients such as preservatives (e.g., sodium benzoate, methyl paraben, ethyl paraben, propyl paraben, and the like), stabilizers (e.g., ferric ammonium citrate, ferrous sulfate, and the like), etc.

The present invention is also directed to a method for increasing the palatability of a liquid vitamin formulation comprising supplementing said formulation with an ester of vitamin D and increasing the water content of said formulation to greater than 252 mg/ml.

The present invention is also directed to a method for increasing the storage stability of a liquid vitamin formulation containing about 320 mg/ml or greater water comprising supplementing said formulation with an ester of vitamin D. The storage stability of the formulation of the invention is improved as compared with a control formulation. It is preferred that the decline in vitamin D activity is improved at least 15% (more preferred is at least 30%, most preferred at least 50%) for the formulation of the invention relative to a control formulation having the same ingredients except for the corresponding non-esterified vitamin D when stored in a sealed container excluding light (e.g., in sealed bottles) at 40° C. for 16 weeks. As an example of a 15% improvement contemplated in the previous sentence, if a control has a 50% decrease in vitamin D activity, a formulation of the invention will have only a 42.5% or less decrease in vitamin D activity.

The invention is further illustrated by the following non-limiting examples. Percentages are by weight/volume unless indicated otherwise.

EXAMPLE 1

A typical liquid vitamin formulation of the invention will have a label claim as follows:

| Ingredient | Quantity Per ml |
| --- | --- |
| Vitamin A | 1500 IU |
| Vitamin $D_3$ | 400 IU |
| Vitamin E | 5 IU |
| Vitamin C | 35 mg |
| Thiamine | 0.5 mg |
| Riboflavin | 0.6 mg |
| Niacin | 8 mg |
| Vitamin $B_6$ | 0.4 mg |
| Vitamin $B_{12}$ | 2 µg |

In addition to the above, the vitamin formulation contains flavorants, stabilizer of vitamins, and about 1.0% polysorbate 80 as surfactant. As appreciated by the skilled artisan, appropriate overages of vitamins are included in order to assure meeting the label claims. The example composition contains 1.86:1 ratio by weight of glycerine to water. The pH is 5.0 which is adjusted by using an appropriate ratio of ascorbic acid to sodium ascorbate.

EXAMPLE 2

Vitamin D Palmitate Preparation

A 10 ml methylene chloride solution containing 1 gm of vitamin $D_3$, 0.78 gm of palmitic acid and 0.03 gm of 4-dimethylaminopyridine was stirred as 0.6 gm of 1,3-dicyclohexylcarbodiimide in methylene chloride was added slowly. The reaction was allowed to proceed for two hours at ambient temperature. Hexane was added, the urea by-product was removed by filtration, and the organic phase was washed with 0.2 N sodium hydroxide, 5% acetic acid in water. The solvents were removed by evaporation under reduced pressure. The product was purified by chromatography through a column of water-deactivated alumina eluted with 1% tetrahydrofuran in hexane. No free vitamin D was detectable in the product which was analyzed to contain 52% vitamin D by spectroscopic absorption at 265 nm. This was confirmed after saponification by HPLC analysis for vitamin D.

EXAMPLE 3

Vitamin D Analyses

Vitamin D was analyzed by a HPLC assay as described by Matthew G. Sliva, et al., "Reversed-Phase Liquid Chromatographic Determination of Vitamin D in Infant Formulas and Enteral Nutritionals," *J Assoc. Off. Anal. Chem.*, 75, 566, 1992, except that saponification conditions of 70° C. for 40 minutes were employed.

Bioactivity (using the official AOAC rat bioassay) was compared to high performance liquid chromatography results; HPLC levels appear to be slightly higher, but not significantly higher, than the bioassay results for both non-esterified and esterified vitamin D.

EXAMPLE 4

Stability Studies

Stability of vitamins $D_3$ and $D_3$ palmitate were compared in various vitamin formulations containing different amounts of water and glycerin and at different pHs. The other ingredients and method of pH adjustment were as described in Example 1. The results are in Tables 2–5. Each batch number represents a different liquid vitamin formulation. The amount of glycerin varied between 650 and 850 mg/ml, depending upon the amount of water. "Vit" represents vitamin, "Desc." represents description, "Vit D3" represents vitamin $D_3$, and "Vit D3P" or "$D_3P$" represents vitamin $D_3$ palmitate. A summary of the stability results of vitamins $D_3$ and $D_3$ palmitate is shown in Table 1. Table 1 lists the half-life ($T_{50}$) values, i.e., time to degrade to 50% of the starting concentration of vitamins $D_3$ and $D_3$ palmitate at 40° C., These $T_{50}$ values were calculated by fitting the data to first order degradation rate. The results are in Table 1.

TABLE 1

Time in Weeks for 50% Degradation of Vitamin $D_3$ or $D_3P$ ($T_{50}$) at 40° C. in Vitamin Formulations at Various pH and Water Content These $T_{50}$ results are based on 16 weeks data at 40° C.

| | $T_{50}$ Values in Weeks for Vitamin $D_3$ or $D_3p$ in Various Vitamin Formulations Water (mg/ml) in the Formulation | | | | | | | |
| --- | --- | --- | --- | --- | --- | --- | --- | --- |
| | 252 | | 320 | | 390 | | 435 | |
| pH | $D_3$ | $D_3P$ | $D_3$ | $D_3P$ | $D_3$ | $D_3P$ | $D_3$ | $D_3P$ |
| 3.2 | 31.4 | 15.2 | — | — | 10.5 | 79.7 | — | — |
| 4.2 | 15.0 | 9.5 | — | — | 6.4 | 42.2 | — | — |
| 5.0 | 16.7 | 9.5 | 12.4 | 14.3 | 5.8 | 61.6 | 5.7 | 24.7 |
| 5.6 | 20.8 | 16.2 | — | — | 6.3 | 26.9 | — | — |

TABLE 2

Short-Term Stability Studies at 40° C. of Liquid Vitamin Formulations at pH 3.2

| | 252 mg/ml water | | 390 mg/ml water | |
| --- | --- | --- | --- | --- |
| Age (weeks) | Vitamin $D_3$ Batch #1 (IU/ml) | Vitamin $D_3P$ Batch #2 (IU/ml) | Vitamin $D_3$ Batch #3 (IU/ml) | Vitamin $D_3P$ Batch #4 (IU/ml) |
| 0 | 787 | 810 | 445 | 430 |
| 0 | 789 | 810 | 447 | 425 |
| 1 | 714 | — | 429 | 404 |
| 1 | 724 | — | 429 | 405 |
| 2 | 718 | 715 | 392 | 405 |
| 2 | 691 | 717 | 399 | 403 |
| 4 | 720 | 668 | 359 | 394 |
| 4 | 713 | 668 | 369 | 397 |
| 6 | 656 | 598 | — | — |
| 6 | 628 | 612 | — | — |
| 8 | 658 | 544 | 282 | 384 |
| 8 | 634 | 574 | 271 | 381 |
| 12 | 514 | 471 | 207 | 374 |
| 12 | 586 | 443 | 211 | 370 |
| 16 | 559 | 397 | 160 | 366 |
| 16 | 542 | 385 | 149 | 362 |

TABLE 3

Short-Term Stability Studies at 40° C. of Liquid Vitamin Formulations at pH 4.2

| | 252 mg/ml water | | 390 mg/ml water | |
| --- | --- | --- | --- | --- |
| Age (weeks) | Vitamin $D_3$ Batch #5 (IU/ml) | Vitamin $D_3P$ Batch #6 (IU/ml) | Vitamin $D_3$ Batch #7 (IU/ml) | Vitamin $D_3P$ Batch #8 (IU/ml) |
| 0 | 450 | 408 | 451 | 414 |
| 0 | 450 | 405 | 448 | 418 |

TABLE 3-continued

Short-Term Stability Studies at 40° C.
of Liquid Vitamin Formulations at pH 4.2

| Age (weeks) | 252 mg/ml water | | 390 mg/ml water | |
|---|---|---|---|---|
| | Vitamin $D_3$ Batch #5 (IU/ml) | Vitamin $D_3P$ Batch #6 (IU/ml) | Vitamin $D_3$ Batch #7 (IU/ml) | Vitamin $D_3P$ Batch #8 (IU/ml) |
| 1 | 440 | 391 | 420 | 397 |
| 1 | 445 | 386 | 418 | 395 |
| 2 | 422 | 368 | 357 | 395 |
| 2 | 425 | 371 | 360 | 399 |
| 4 | 364 | 314 | 301 | 379 |
| 4 | 371 | 316 | 299 | 371 |
| 8 | 331 | 234 | 181 | 353 |
| 8 | 315 | 234 | 178 | 347 |
| 12 | 255 | 145 | 109 | 339 |
| 12 | 267 | 146 | 124 | 328 |
| 16 | 198 | 145 | 91.7 | 319 |
| 16 | 224 | 144 | 76.1 | 315 |

TABLE 4

Short-Term Stability Studies at 40° C.
of Liquid Vitamin Formulations at pH 5.0

| Age (weeks) | 252 mg/ml water | | 390 mg/ml water | |
|---|---|---|---|---|
| | Vitamin $D_3$ Batch #9 (IU/ml) | Vitamin $D_3P$ Batch #10 (IU/ml) | Vitamin $D_3$ Batch #11 (IU/ml) | Vitamin $D_3P$ Batch #12 (IU/ml) |
| 0 | 840 | 426 | 454 | 433 |
| 0 | 851 | 424 | 449 | 437 |
| 1 | 791 | 394 | 432 | 404 |
| 1 | 793 | 397 | 423 | 414 |
| 2 | — | 363 | 424 | 380 |
| 2 | — | 363 | 426 | 383 |
| 4 | 720 | 335 | 377 | 364 |
| 4 | 700 | 329 | 371 | 364 |
| 8 | 583 | 244 | 291 | 306 |
| 8 | 590 | 244 | 281 | 300 |
| 12 | 478 | 201 | 230 | 264 |
| 12 | 482 | 193 | 237 | 263 |
| 16 | 460 | 123 | 196 | 188 |
| 16 | 430 | 125 | 182 | 186 |

| Age (weeks) | 390 mg/ml water | | 435 mg/ml water | |
|---|---|---|---|---|
| | Vitamin $D_3$ Batch #13 (IU/ml) | Vitamin $D_3P$ Batch #14 (IU/ml) | Vitamin $D_3$ Batch #15 (IU/ml) | Vitamin $D_3P$ Batch #16 (IU/ml) |
| 0 | 453 | 593 | 450 | 431 |
| 0 | 452 | 599 | 453 | 433 |
| 1 | 413 | 573 | 400 | 418 |
| 1 | 410 | 570 | 426 | — |
| 2 | 363 | — | 370 | 395 |
| 2 | 356 | — | 370 | 404 |
| 4 | 298 | 554 | 285 | 403 |
| 4 | 305 | 555 | 291 | 394 |
| 8 | 166 | 510 | 187 | 364 |
| 8 | 168 | 500 | 170 | 364 |
| 12 | 100 | 525 | 107 | 343 |
| 12 | 107 | 508 | 103 | 338 |
| 16 | 60.8 | 490 | — | 256 |
| 16 | 84.3 | 492 | — | 256 |

TABLE 5

Short-Term Stability Studies at 40° C.
of Liquid Vitamin Formulations at pH 5.6

| Age (weeks) | 252 mg/ml water | | 390 mg/ml water | |
|---|---|---|---|---|
| | Vitamin $D_3$ Batch #17 (IU/ml) | Vitamin $D_3P$ Batch #18 (IU/ml) | Vitamin $D_3$ Batch #19 (IU/ml) | Vitamin $D_3P$ Batch #20 (IU/ml) |
| 0 | 439 | 418 | 450 | 424 |
| 0 | 438 | 421 | 454 | 416 |
| 1 | 441 | 385 | 420 | 396 |
| 1 | 442 | 400 | 438 | 395 |
| 2 | 411 | 371 | 369 | 396 |
| 2 | 396 | 371 | 377 | 400 |
| 4 | 390 | 338 | 317 | 374 |
| 4 | 394 | 330 | 307 | 370 |
| 8 | 333 | 286 | 193 | 341 |
| 8 | 354 | 287 | 184 | — |
| 12 | 310 | 232 | 110 | 295 |
| 12 | 300 | 237 | 114 | 302 |
| 16 | 245 | 214 | 87.5 | 279 |
| 16 | 265 | 212 | 82.5 | 276 |

I claim:

1. A liquid vitamin formulation at an acidic pH comprising per ml of composition an ester of antirachitic vitamin D, greater than 252 mg/ml water and at least about 100 mg/ml polyhydroxylated solvent, wherein said ester of antirachitic vitamin D is esterified at carbon 3.

2. The vitamin formulation of claim 1 at a pH of about 6 or less.

3. The vitamin formulation of claim 1 at a pH of between 3 and about 6.

4. The vitamin formulation of claim 1 at a pH of between about 3.2 and about 5.6.

5. The vitamin formulation of claim 1 comprising between about 500 and about 950 mg/ml polyhydroxylated solvent.

6. The vitamin formulation of claim 1 comprising between about 550 and about 850 mg/ml polyhydroxylated solvent.

7. The vitamin formulation of claim 1 wherein said polyhydroxylated solvent is glycerine, sorbitol, polyethylene glycol, or a mixture thereof.

8. The vitamin formulation of claim 1 wherein said polyhydroxylated solvent is glycerine.

9. The vitamin formulation of claim 1 comprising at least about 320 mg/ml water.

10. The vitamin formulation of claim 1 comprising about 280 to about 550 mg/ml water.

11. The vitamin formulation of claim 1 comprising about 320 to about 550 mg/ml water.

12. The vitamin formulation of claim 1 comprising about 320 to about 550 mg/ml water.

13. The vitamin formulation of claim 1 comprising about 350 to about 430 mg/ml water.

14. The vitamin formulation of claim 1 comprising about 370 to about 410 mg/ml water.

15. The vitamin formulation of claim 1 at a pH of about 5 and comprising about 350 to about 430 mg/ml water and about 100 to about 850 mg/ml polyhydroxylated solvent.

16. The vitamin formulation of claim 1 additionally comprising at least one vitamin selected from the group consisting of thiamine, riboflavin, niacin, vitamin $B_6$, vitamin C, vitamin $B_{12}$, vitamin A, and vitamin E.

17. The vitamin formulation of claim 1 wherein said ester of vitamin D is an ester of vitamin $D_3$.

18. The vitamin formulation of claim 1 wherein said ester of vitamin D is a fatty acid ester of vitamin D.

19. The vitamin formulation of claim 1 wherein said ester of vitamin D is a fatty acid ester of vitamin $D_3$.

20. The vitamin formulation of claim 17 wherein the fatty acid moiety contains between 2 and 20 carbon atoms.

21. The vitamin formulation of claim 17 wherein the fatty acid moiety contains between 8 and 18 carbon atoms.

22. The vitamin formulation of claim 17 wherein the fatty acid moiety contains between 14 and 18 carbon atoms.

23. The vitamin formulation of claim 1 wherein said ester of vitamin D is vitamin D acetate, vitamin D propionate, vitamin D myristate, vitamin D palmitate, vitamin D stearate, vitamin D oleate, vitamin D linolenate, vitamin D arachidonate, vitamin D linoleate, vitamin D caprate, vitamin D caproate, vitamin D laureate, vitamin D eicosapentaenoate, vitamin D docosahexaenoate, vitamin D benzoate, vitamin D lactate, vitamin D sorbate, vitamin D glycinate, vitamin D alanate, vitamin D succinate, vitamin D fumarate, vitamin D polyethylene glycol succinate, vitamin D sulfate, vitamin D phosphate, or a mixture thereof.

24. The vitamin formulation of claim 1 wherein said ester of vitamin D is vitamin $D_3$ acetate, vitamin $D_3$ propionate, vitamin $D_3$ myristate, vitamin $D_3$ palmitate, vitamin $D_3$ stearate, vitamin $D_3$ oleate, vitamin $D_3$ linolenate, vitamin $D_3$ arachidonate, vitamin $D_3$ linoleate, vitamin $D_3$ caprate, vitamin $D_3$ caproate, vitamin $D_3$ laureate, vitamin $D_3$ eicosapentaenoate, vitamin $D_3$ docosahexaenoate, vitamin $D_3$ benzoate, vitamin $D_3$ lactate, vitamin $D_3$ sorbate, vitamin $D_3$ glycinate, vitamin $D_3$ alanate, vitamin $D_3$ succinate, vitamin $D_3$ fumarate, vitamin $D_3$ polyethylene glycol succinate, vitamin $D_3$ sulfate, vitamin $D_3$ phosphate, or a mixture thereof.

25. The vitamin formulation of claim 1 wherein said ester of vitamin D is vitamin $D_3$ palmitate.

26. The vitamin formulation of claim 1 wherein said ester of vitamin D is present in an amount of between about 200 and about 1000 IU/ml.

27. The vitamin formulation of claim 1 wherein said ester of vitamin D is present in an amount of between about 360 and about 800 IU/ml.

28. The vitamin formulation of claim 1 comprising at least about 90% of the RDA per ml of composition for at least one vitamin selected from the group consisting of vitamin A, vitamin D, vitamin E, vitamin C, thiamine, riboflavin, niacin, vitamin $B_6$ and vitamin $B_{12}$.

29. The vitamin formulation of claim 1 comprising at least about 100% of the RDA per ml of composition for at least one vitamin selected from the group consisting of vitamin A, vitamin D, vitamin E, vitamin C, thiamine, riboflavin, niacin, vitamin $B_6$ and vitamin $B_{12}$.

30. The vitamin formulation of claim 1 at an osmolality of about 7000 to about 9000 mOsm/kg $H_2O$.

31. A liquid vitamin formulation at a pH of between about 3.2 and about 5.6 comprising per ml of composition about 200 to about 1000 IU of a fatty acid ester of antirachitic vitamin $D_3$ esterified at the 3 carbon, about 500 to about 950 mg/ml glycerin, and about 280 to about 550 mg/ml water.

32. The vitamin formulation of claim 31 at a pH of about 5 wherein said fatty acid ester of vitamin $D_3$ is vitamin $D_3$ palmitate, wherein the amount of water is about 350 mg/ml, and wherein said formulation additionally comprises at least about 100% of the RDA per ml of composition for at least one vitamin selected from the group consisting of vitamin A, vitamin D, vitamin E, vitamin C, thiamine, riboflavin, niacin, vitamin $B_6$ and vitamin $B_{12}$.

* * * * *